United States Patent
Asano et al.

(10) Patent No.: US 12,233,045 B2
(45) Date of Patent: Feb. 25, 2025

(54) THERAPEUTIC AGENT FOR TREATING BRADYARRHYTHMIA

(71) Applicants: OSAKA UNIVERSITY, Suita (JP); NISSAN CHEMICAL CORPORATION, Tokyo (JP)

(72) Inventors: Yoshihiro Asano, Suita (JP); Seiji Takashima, Suita (JP); Noriaki Yamada, Suita (JP); Toru Yamashita, Tokyo (JP)

(73) Assignees: OSAKA UNIVERSITY, Osaka (JP); NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 18/134,609

(22) Filed: Apr. 14, 2023

(65) Prior Publication Data

US 2023/0248694 A1 Aug. 10, 2023

Related U.S. Application Data

(62) Division of application No. 17/419,100, filed as application No. PCT/JP2019/051456 on Dec. 27, 2019, now abandoned.

(30) Foreign Application Priority Data

Dec. 28, 2018 (JP) ................. 2018-247919

(51) Int. Cl.
*A61K 31/353* (2006.01)
*A61K 31/4741* (2006.01)
*A61P 9/06* (2006.01)

(52) U.S. Cl.
CPC ........ *A61K 31/353* (2013.01); *A61K 31/4741* (2013.01); *A61P 9/06* (2018.01)

(58) Field of Classification Search
CPC ...... A61K 31/4741; A61K 31/353; A61P 9/06
See application file for complete search history.

(56) References Cited

U.S. PATENT DOCUMENTS

| | | |
|---|---|---|
| 7,781,483 B2 | 8/2010 | Tsukagoshi et al. |
| 2008/0004262 A1 | 1/2008 | Ohrai et al. |
| 2010/0069374 A1* | 3/2010 | Ohrai ............ C07D 513/04 514/224.5 |

FOREIGN PATENT DOCUMENTS

| | | |
|---|---|---|
| JP | H08-268891 A | 10/1996 |
| JP | 2001-151767 A | 6/2001 |
| JP | 2007-530436 A | 11/2007 |
| JP | 2010-136660 A | 6/2010 |
| WO | 01/21610 A1 | 3/2001 |
| WO | 2005/090357 A1 | 9/2005 |

OTHER PUBLICATIONS

Mar. 31, 2020 International Search Report issued in International Patent Application No. PCT/JP2019/051456.
Mar. 31, 2020 Written Opinion issued in International Patent Application No. PCT/JP2019/051456.
Norio Hashimoto; "Application of Selective Acetylcholine-Sensitive K+-Channel Blockade as a Therapeutic Strategy for Atrial Fibrillation"; Folia Pharmacologica Japonica, 2010, vol. 136, pp. 77-82, Fig. 2-3.
Yoshinori Kobayashi; "Clinical Characteristics and Management of Proarrhythmias During Antiarrhythmic Therapy"; Japanese Journal of Clinical Medicine, 2013, vol. 71, No. 1, pp. 79-85.
Jan. 20, 2023 Office Action issued in U.S. Appl. No. 17/419,100.
Oct. 4, 2023 Office Action issued in Japanese Patent Application No. 2020-562502.
Oct. 14, 2024 Office Action issued in Chinese Patent Application No. 201980093223.8.
Pandlife et al., "Study of Clinical Presentations and Treatment Strategies with Special Cervical Hypertension," Chinese Commerce Press, p. 95, Sep. 30, 2009.

* cited by examiner

*Primary Examiner* — Marcos L Sznaidman
(74) *Attorney, Agent, or Firm* — Oliff PLC

(57) ABSTRACT

A method of treating bradyarrhythmia includes administering to a patient having bradyarrhythmia a therapeutically effective amount of at least one of compound (I) and compound (II) or pharmacologically acceptable salts thereof as an active component:

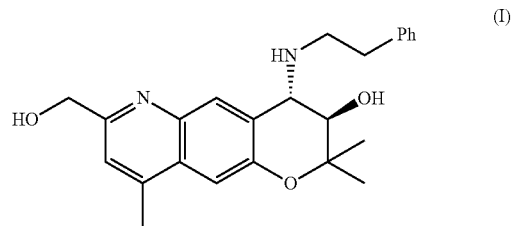

(I)

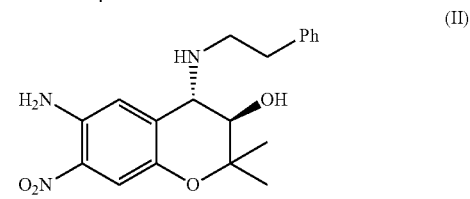

(II)

wherein Ph is a phenyl group.

14 Claims, 7 Drawing Sheets

FIG. 9
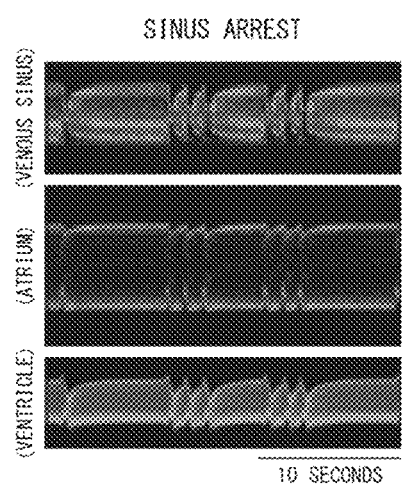
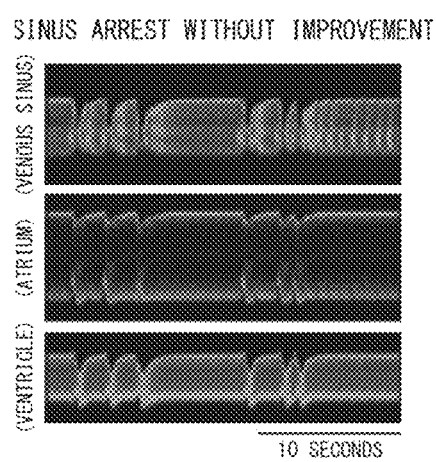

THERAPEUTIC AGENT FOR TREATING BRADYARRHYTHMIA

The present application is a divisional application of U.S. patent application Ser. No. 17/419,100 filed Jun. 28, 2021, which is a U.S. national stage application of PCT/JP2019/051456 filed Dec. 27, 2019, claiming priority to Japanese App. No. 2018-247919 filed Dec. 28, 2018. Each of these prior applications is incorporated herein by reference in its entirety.

TECHNICAL FIELD

The present invention relates to a therapeutic agent for bradyarrhythmia.

BACKGROUND ART

Arrhythmias are conditions in which the heart rate or heart pulsation rhythm is irregular, and have various electrocardiographic abnormalities. Arrhythmia due to abnormal heart rate can be classified into tachyarrhythmia and bradyarrhythmia. The heart rate of humans at rest is generally about 50 beats min to 100 beats/min, bradycardia is a heart rate lower than that and tachycardia is a heart rate higher than that. Examples of bradyarrhythmias include sick sinus syndrome (SSS), atrioventricular block (A-V block), atrioventricular dissociation (A-V dissociation), and junctional rhythm.

Sick sinus syndrome is a disease in which the pulse is slowed mainly due to decline of sinus node functions, and as a result, dysfunction of the brain, heart, kidney, and the like is observed. Electrocardiographically, it is classified into three types: 1) sinus bradycardia (heart rate 50 beats per minute or less), 2) sinus arrest or sinoatrial block, and 3) bradycardia tachycardia syndrome. Clinically, symptoms such as Adam-Stokes attacks, heart failure, and easy fatigability appear chronically. As a treatment method, in order to increase the number of spontaneous excitements of the sinus node, oral drugs and intravenous injection agents, such as an anticholinergic agent (atropine sulfate), and a β stimulant may be used, and if bradycardia is not improved with these administrations, or if symptoms worsen when drug administration is discontinued, a pacemaker may be used.

The sinus node, which is the beginning of electrical stimulation in the heart, is a tissue in which a part of the myocardium is specialized and has an acquired automatic ability, and specific proteins are expressed therewith. Among these, the most important function for the sinus node is that of a cell membrane protein group called a channel. Channels contribute to formation of electric potential gradients inside and outside cells by allowing ions to permeate through the cell membrane, and not just for the sinus node, are involved in the most important functions of the heart which are the propagation of electronic signals in all cardiomyocytes, and subsequent contraction of the heart.

It has long been known that abnormalities in channel genes cause arrhythmias, and according to recent advances in genetic analysis technology, some channel genes have been identified as causative genes associated with arrhythmias.

In recent years, the inventors have analyzed genes associated with bradycardias in family members with congenital bradycardia, and identified a new gene mutation of KCNJ3, which is one G protein-regulated potassium channel among important channels for sinus node functions. For patients with an abnormally slow pulse phenotype, informed consent from the patients and approval from the institution's ethics committee were obtained and the patients and their families were then genetically analyzed, and as a result, it was confirmed that the presence of the phenotype of bradycardia in the families is linked to the presence of the same gene mutation of KCNJ3. This mutation corresponds to the change of the 83rd amino acid from the N-terminus of a KCNJ3 protein, which is a gene product of KCNJ3, from asparagine (N) to histidine (H) (hereinafter sometimes referred to as "KCNJ3 N83H"). The phenotype of KCNJ3 N83H exhibits bradycardia, which suggested that the mutation of KCNJ3 genes related to KCNJ3 N83H is dominantly inherited (for example, refer to Patent Document 1).

The KCNJ3 protein, which is a gene product of KCNJ3, constitutes a cardiac acetylcholine-activated potassium channel (KACh channel or Kir3.1/3.4 channel) as a heterotetramer together with KCNJ5. When acetylcholine is released from the vagus nerve termination, the KACh channel opens according to activation of M2 receptors, which are muscarinergic acetylcholine receptors, potassium ions flow out of the cell, and thus the heart rate is reduced. In an experiment according to a two-electrode voltage clamp method using *Xenopus laevis* oocytes, it was confirmed that, both before and after acetylcholine (ACh) was added, the mutant (KCNJ3 N83H) KACh channel makes a current 5 to 10 times more likely to flow than the wild type (KCNJ3 WT) KACh channel, and the mutant channel had greater channel activity.

This KCNJ3 mutation-induced disease has been newly defined as one of inherited bradyarrhythmias. This disease can also be called KACh channelopathy or Kir3.1/3.4 channelopathy. This disease is a rare arrhythmia in which bradycardia reduces the cardiac output required to maintain the biological function and reduces the physical activity and quality of life. In addition, this disease has serious risks such as low cardiac output heart failure, loss of consciousness, and sudden death as it progresses.

As described above, the KACh channelopathy is an inherited bradyarrhythmia caused by a mutation of KCNJ3, and it is expected that a modulator (agonist or antagonist) for KCNJ3 would improve pathological conditions thereof. However, a specific compound having a therapeutic effect on bradyarrhythmia targeting the KACh channel has not been reported until now.

In addition, it is also unclear what kind of modulator is effective for treatment. It is difficult to predict whether a human wild-type KCNJ3 modulator will also be effective for "KCNJ3 N83H."

PRIOR ART DOCUMENTS

Patent Document

[Patent Document 1] Japanese Unexamined Patent Application Publication No. 2010-136660 (JP 2010-136660 A)

SUMMARY OF THE INVENTION

Problem to be Solved by the Invention

An object of the present invention is to provide a novel therapeutic agent for bradyarrhythmia.

Means for Solving the Problem (3R4S)-7-hydroxymethyl-2,2,9-trimethyl-4-(phenethyl-amino)-3,4-dihydro-2H-pyra no[2,3-g]quinoline-3-ol (hereinafter referred to as a compound (I)) is a compound having a therapeutic effect on atrial fibrillation (refer to WO 2005/090357, etc.). The inventors have found that the compound (I) has an inhibitory action on a human wild-type KACh channel (hereinafter, sometimes referred to as "KCNJ3 WT KACh channel") composed of a human wild-type KCNJ3 protein which is a gene product of human wild-type KCNJ3 and a human wild-type KCNJ5 protein which is a gene product of human wild-type KCNJ5.

In addition, (3R,4S)-6-amino-3,4-di hydro-2,2-dimethyl-7-nitro-4-(2-phenethyl amino)-2H-1-benzopyran-3-ol (hereinafter, also referred to as a compound (II), and the compounds (I) and (II) together are referred to as the compound of the present invention) is a compound that has an atrial-selective refractory period prolonging action and has been reported to be effective against arrhythmia (refer to WO 01/21610, etc.). The inventors have found that the compound (II) has an inhibitory action on the "KCNJ3 WT KACh channel."

As described above, it is known that the compound of the present invention has an anti-atrial fibrillation action according to an inhibitory action on the KCNJ3 WT KACh channel. However, it can be said that atrial fibrillation, which is a particularly fast tachycardia among tachycardia diseases, and inherited bradyarrhythmia, which is a bradycardic disease, are almost directly opposite pathological conditions. In addition, it was unclear whether the compound of the present invention had an inhibitory action on the mutant KACh channel (hereinafter sometimes referred to as "KCNJ3 N83H KACh channel") composed of a KCNJ3 N83H protein and a human wild-type KCNJ5 protein. Therefore, it has been difficult to predict whether the compound of the present invention will be a therapeutic agent for inherited bradyarrhythmia.

However, the inventors conducted extensive studies and as a result, surprisingly, found that the compound of the present invention exhibited a stronger inhibitory action on the "KCNJ3 N83H KACh channel" than on the "KCNJ3 WT KACh channel."

In addition, as a result of studies by the inventors, it was clarified that the KACh channelopathy exhibited various pathological conditions such as sinus arrest, sinoatrial block, and atrioventricular block in addition to sinus bradycardia. In the conventional arrhythmia treatment, no existing drugs are known to be effective for all of these various pathological conditions with one kind of drug.

However, the inventors conducted extensive studies and as a result, surprisingly, found that the compound of the present invention exhibited a strong inhibitory effect on all pathological conditions such as sinus bradycardia, sinus arrest, sinoatrial block, and atrioventricular block derived from the "KCNJ3 N83H KACh channel" in a zebrafish model, and clarified that the compound of the present invention may be a first agent for inherited bradyarrhythmia (KACh channelopathy) caused by a mutation of KACh channel genes.

In addition, as a result of studies by the inventors, also in a wild type zebrafish model, the compound of the present invention increased the heart rate. That is, it was confirmed that the compound of the present invention was also effective for bradycardia not caused by a KACh channel mutation.

In addition, it was confirmed that the compound of the present invention was also effective for arrhythmia caused by a mutation in a KCNJ5 protein, particularly, bradyarrhythmia caused by a mutation in the 101st amino acid from the N-terminus of the KCNJ5 protein from tryptophan (W) to cysteine (C).

Therefore, the present invention is as follows.

(1) A therapeutic agent for bradyarrhythmia containing the following compound (I) or compound (II) or a pharmacologically acceptable salt thereof as an active component:

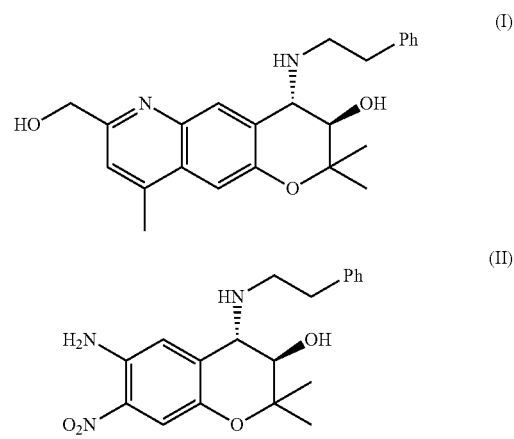

(wherein, Ph is a phenyl group)

(2) The therapeutic agent according to (1), wherein the bradyarrhythmia is inherited bradyarrhythmia.

(3) The therapeutic agent according to (1), wherein the bradyarrhythmia is any of sinus bradycardia, sinus arrest, sinoatrial block and atrioventricular block.

(4) The therapeutic agent according to (1), wherein the bradyarrhythmia is any of sinus bradycardia, sinus arrest, sinoatrial block and atrioventricular block and is inherited bradyarrhythmia.

(5) The therapeutic agent according to any one of (1) to (4), containing the following compound (I) or a pharmacologically acceptable salt thereof as an active component:

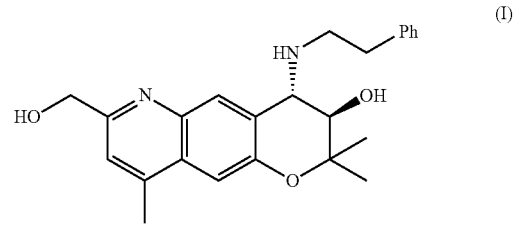 [SMILES: Cc1cc(CO)nc2cc3c(cc12)OC(C)(C)[C@H](O)[C@H]3NCCc1ccccc1]

(wherein, Ph is a phenyl group).

(6) The therapeutic agent according to any one of (1) to (4), containing the following compound (II) or a pharmacologically acceptable salt thereof as an active component:

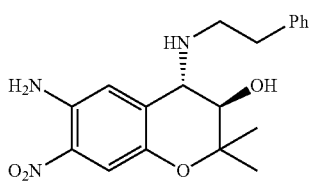

(II)

(wherein, Ph is a phenyl group).

(7) The therapeutic agent according to any one of (1) to (6), wherein
the bradyarrhythmia is an arrhythmia caused by a mutation in the 83rd amino acid from the N-terminus of a KCNJ3 protein from asparagine (N) to histidine (H).

(8) The therapeutic agent according to any one of (1) to (6), wherein
the bradyarrhythmia is an arrhythmia caused by a mutation in the 101st amino acid from the N-terminus of a KCNJ5 protein from tryptophan (W) to cysteine (C).

Effects of the Invention

The present invention provides a therapeutic agent for bradyarrhythmia.

BRIEF DESCRIPTION OF THE DRAWINGS

FIG. 9 shows images obtained by detailed analysis of the heart rate and pulsation rhythm using analysis software based on the video of sinus venosus, atrium and ventricle pulsations before and 1 hour after application of 100 nM of Tertiapin-Q to KCNJ3 N83H mutant zebrafish causing sinus arrest.

MODES FOR CARRYING OUT THE INVENTION

Figure 1:
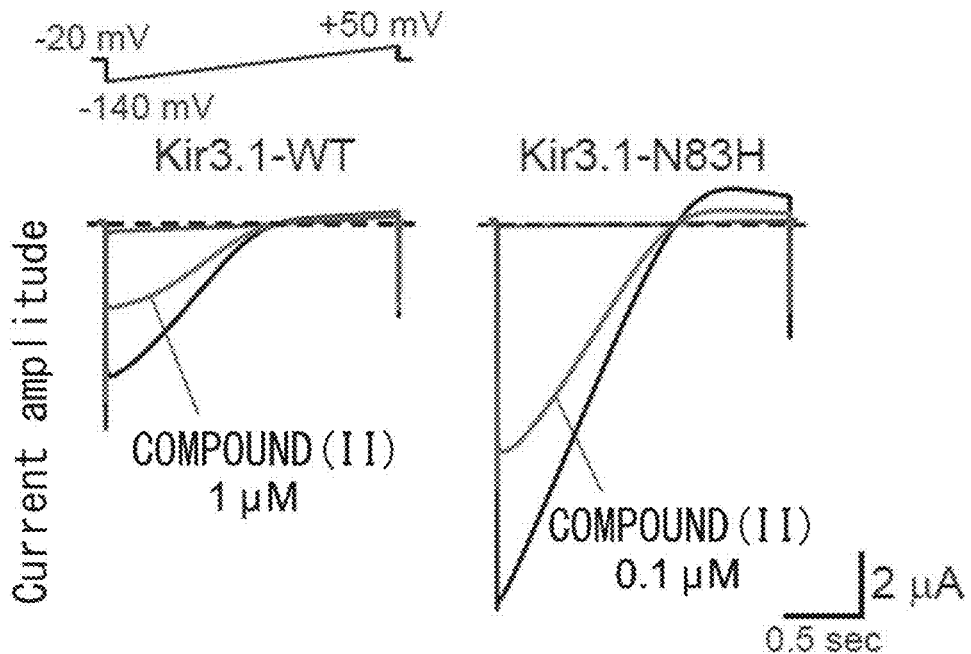
FIG. 1 shows graphs showing changes in current amplitude of a KCNJ3 WT KACh channel (Kir3.1-WT) and a KCNJ3 N83H KACh channel (Kir3.1-N83H) expressed in *Xenopus laevis* oocytes due to a compound (II), which are detected using a two-electrode voltage clamp method.

Inherited bradyarrhythmias are inherited bradycardic arrhythmias observed in families with congenital bradycardia. It has been confirmed by the inventors that the inherited bradyarrhythmia in families is linked to the presence of a gene mutation in KCNJ3. More specifically, it has been confirmed that this mutation is a mutation in the 83rd amino acid from the N-terminus of a KCNJ3 protein, which is a gene product of KCNJ3, from asparagine (N) to histidine (H). The KACh channelopathy or Kir3.1/3.4 channelopathy is understood as one new pathological condition of inherited bradycardic arrhythmia.

Therefore, inherited bradyarrhythmia in the present invention can be understood as being the diseases mentioned below (1) Bradyarrhythmia caused by a mutation in KCNJ3.
(2) Bradyarrhythmia caused by a mutation in the 83rd amino acid from the N-terminus of the KCNJ3 protein.
(3) Bradyarrhythmia caused by a mutation in the 83rd amino acid from the N-terminus of the KCNJ3 protein from asparagine (N) to histidine (H)
(4) Disease according to any one of (1) to (3) in which bradyarrhythmia is sinus bradycardia, sinus arrest, sinoatrial block or atrioventricular block.

In the present invention, sinus bradycardia is a pathological condition in which the pulsation rhythm is normal and regular but the heart rate slows down among arrhythmia symptoms. Generally, sinus bradycardia is understood as a pathological condition in which the heart rate decreases to 50 beats or less per minute. Sinus bradycardia is understood as a pathological condition of Group 1 among sick sinus syndromes according to Rubenstein classification.

In the present invention, sinus arrest is a pathological condition in which no electronic signal is generated from the sinus node and atrial excitement does not occur.

In the present invention, sinoatrial block is a pathological condition in which atrial excitement does not occur due to impulse conduction disorder between the sinus node and the atrium.

In the present invention, atrioventricular block is a pathological condition in which ventricular excitement does not occur due to impulse conduction disorder between the atrium and the ventricle. Atrioventricular block includes the following disease type classifications.
  (1) First-degree atrioventricular block
      A conduction time between the atrium and the ventricle is prolonged (conduction of excitement is maintained)
  (2) Second-degree atrioventricular block: the conduction between the atrium and the ventricle is suddenly interrupted. It includes the following two types.
  (2-1) Wenckebach type: excitement of the ventricle is lost after the conduction between the atrium and the ventricle is gradually prolonged.
  (2-2) Mobitz type II: excitement of the ventricle is suddenly lost without prolonging of conduction between the atrium and the ventricle.
  (2-3) Advanced atrioventricular block: atrioventricular conduction is rarely observed.
  (3) Third-degree atrioventricular block: the conduction between the atrium and the ventricle is completely interrupted.

KCNJ3 is one of human genes, and a KCNJ3 protein, which is a gene product of KCNJ13, constitutes a cardiac acetylcholine-activated potassium channel (KACh channel or Kir3.1/3.4 channel) as a heterotetramer together with a KCNJ5 protein.

Here, the KCNJ3 protein is also called Kir3.1 or GIRK1, and the KCNJ5 protein is also called Kir3.4 or GIRK4.

In the present invention, as described above, KCNJ3 N83H means that the 83rd amino acid from the N-terminus of the KCNJ3 protein, which is a gene product of KCNJ3, is changed from asparagine (N) to histidine (H).

Patients targeted by the therapeutic agent of the present invention are not limited as long as this therapeutic agent is effective. More specifically, patients targeted by the therapeutic agent of the present invention are one of the following patients.
  (1) Patients with possible inherited bradyarrhythmia
  (2) Patients diagnosed with inherited bradyarrhythmia
  (3) Patients with a mutation in a KCNJ3 gene
  (4) Patients with a mutation in the 83rd amino acid from the N-terminus of the KCNJ3 protein
  (5) Patients with the 83rd amino acid from the N-terminus of the KCNJ3 protein having been changed from asparagine (N) to histidine (H)
  (6) Patients with a mutation in a KCNJ5 gene
  (7) Patients with inherited bradycardic arrhythmia
  (8) Patients with bradyarrhythmia
  (9) Patients with arrhythmia Diseases targeted by the therapeutic agent of the present invention are not limited as long as this therapeutic agent is effective therefor. Symptoms targeted by the therapeutic agent of the present invention include the following.
  (1) arrhythmia, (2) bradyarrhythmia, (3) sinus bradycardia, (4) sinus arrest, (5) sinoatrial block, (6) atrioventricular block, (7) sinus node dysfunction, (8) bradycardic heart failure.

As a result of genetic analysis of patients with an abnormally slow pulse phenotype and their family members, the presence bradycardia phenotype in the family members is linked to the presence of the same gene mutation in KCNJ3.

The inventors also identified rare mutations other than N83H for KCNJ3 and KCNJ5. These mutations may also be involved in arrhythmia pathological conditions.

Mutations other than N83H are (1) KCNJ3 F85L, (2) KCNJ3 N496H, (3) KCNJ5 D262G, (4) KCNJ5 V303I, and (5) KCNJ5 G387R.

Here, in addition to the above Patent Document 1 (Japanese Unexamined Patent Application Publication No. 2010-136660 (JP 2010-136660 A), after the priority date of the present invention; an example of inherited bradyarrhythmia due to a mutation in the GIRK channel, particularly, a mutation in KCNJ5, has been reported (refer to Circ Genom Precis Med. 2019; 12: e002238 published Jan. 15, 2019). As described above, arrhythmia caused by this mutation in KCNJ5 is also a treatment target of the present invention.

In another aspect, mutations other than N83H are (6) KCNJ5 W101C.

The compound of the present invention shown in this specification may also have a therapeutic effect on arrhythmia caused by the above mutations (1) to (6).

Here, the effect of the compound of the present invention on the above mutations (1) to (6) may be synergistic, additive, or different from the effect on the N83H mutation in KCNJ3.

Therefore, diseases targeted by the therapeutic agent of the present invention include the following arrhythmias in addition to the bradyarrhythmia caused by the N8314 mutation in KCNJ3 described above (also described here as (A))
  (A1) Arrhythmia caused by a mutation in the 85th amino acid from the N-terminus of the KCNJ3 protein from (F) to (L).
  (A2) Arrhythmia caused by a mutation in the 496th amino acid from the N-terminus of the KCNJ3 protein from (N) to (H).
  (B) Arrhythmia caused by a mutation in KCNJ5
  (B1) Arrhythmia caused by a mutation in the 262nd amino acid from the N-terminus of the KCNJ5 protein from (D) to (G).
  (B2) Arrhythmia caused by a mutation in the 303rd amino acid from the N-terminus of the KCNJ5 protein from (Y) to (I).
  (B3) Arrhythmia caused by a mutation in the 387th amino acid from the N-terminus of the KCNJ5 protein from (G) to (R).

Among these five arrhythmias, the more important diseases are (A2) and (B1), and atrial fibrillation is particularly assumed as the arrhythmia.

In another aspect, diseases targeted by the therapeutic agent of the present invention include the following arrhythmias in addition to bradyarrhythmia caused by the N83H mutation in KCNJ3 described above.
  (B4) arrhythmia caused by a mutation in the 101st amino acid from the N-terminus of the KCNJ5 protein from tryptophan (W) to cysteine (C).

Disease (B4) is also important, and bradyarrhythmia is assumed as the arrhythmia.

Therefore, detailed aspects of patients targeted by the therapeutic agent of the present invention described above also include the following.
  (10) Patients with the 101st amino acid from the N-terminus of the KCNJ5 protein having been changed from tryptophan (W) to cysteine (C).

Here, to avoid ambiguity, the one-letter notations of amino acids in the above description are supplemented as follows. F: phenylalanine, L: leucine, N: asparagine, H: histidine, D: aspartic acid, G: glycine, V: valine, I: isoleucine, R: arginine, W: tryptophan, C: cysteine.

As described above, a compound (I) contained in the therapeutic agent of the present invention is (3R,4S)-7-hydroxymethyl-2,2,9-trimethy-4-(phenethy amino)-3,4-dihydro-2H-pyrano[2, 3-g] quinoline-3-ol.

In one aspect, the compound (I) may be a racemic mixture or diastereomer mixture containing a (3R,4S) form.

In another aspect, the compound contained in the therapeutic agent of the present invention may be an analogue of the compound (I). Examples of the analogue include the compound described in WO 2005/090357.

As described above, a compound (II) contained in the therapeutic agent of the present invention is (3R,4S)-6-amino-3,4-dihydro-2,2-dimethyl-7-nitro-4-(2-phenethyl-amino)-211-1-benzopyr an-3-ol.

In one aspect, the compound (II) may be a racemic mixture or diastereomer mixture containing a (3R/4S) form.

In another aspect, the compound contained in the therapeutic agent of the present invention may be an analogue of the compound (II). Examples of the analogue include the compound described in WO 01/21610.

The compounds (I) and (II) contained in the therapeutic agent of the present invention may be in the form of a pharmacologically acceptable salt.

Examples of pharmacologically acceptable salts include a hydrochloride, hydrobromide, sulfate, methanesulfonate, acetate, benzoate, tartrate, phosphate, lactate, maleate, fumarate, malate, gluconate and salicylate.

Preferable salts of the compound (1) are a hydrochloride, maleate, and methanesulfonate.

Preferable salts of the compound (II) are hydrochlorides.

The compound contained in the therapeutic agent of the present invention may be a crystal. The crystal may have any crystal form as long as it does not interfere with the object of the present invention, Examples of preferable crystal forms of the compound (I) include crystal forms described in WO 2010/126138. In one aspect, the crystal is a crystal having a characteristic peak at a diffraction angle 2 θ=5.6, 8.2, 12.0, 14.7, 16.6, 16.9, 17.9, 18.4, 22.5, 24.5, 27.6 (±0.2°) as a powder x-ray diffraction pattern when Cu:Kα is used as an X-ray source. In another aspect, the crystal is a crystal having any 3, 5, 7 or 9 peaks among the 11 peaks. Identification of the crystal form by powder x-ray diffraction is performed based on common technical knowledge of those skilled in the art, for example, description of Japanese Pharmacopoeia. When X rays other than Cu·Kα rays are used, diffraction angle patterns are compared according to conversion of the 2θ value based on the Bragg's equation. The measurement error of the 2θ value is generally in a range of ±0.2°, but even if there are a small number of peaks having an error of 0.2° or more, it does not hinder rational identification for those skilled in the art.

The compound (I) contained in the therapeutic agent of the present invention can be produced by a known method. The known methods include, for example, WO 2005/090357 and WO 2010/126138. In addition, in order to produce the compound (I), WO 2007/105658, WO 2014/050613, WO 2014/051077, WO 2015/012271, and the like can be referred to.

The compound (II) contained in the therapeutic agent of the present invention can be produced by a known method in WO 01/21610 or the like.

The present invention provides a pharmaceutical composition or veterinary pharmaceutical composition containing an amount of the compound of the present invention effective for the treatment.

Examples of dosage forms of the compound according to the present invention include parenteral administration with injection agents (subcutaneous, intravenous, intramuscular, intraperitoneal injection), ointments, suppositories, aerosol agents, and the like or oral administration with tablets, capsules, granules, pills, syrups, liquids, emulsions, suspensions, and the like.

The pharmaceutical or veterinary pharmaceutical composition containing the compound according to the present invention contains about 0.01% to 99.5%, and preferably about 0.1% to 30% of the compound according to the present invention with respect to the weight of the whole composition.

In addition to the compound according to the present invention or a composition containing the compound, other pharmaceutical or veterinarily pharmaceutical active compounds can be included.

In addition, these compositions can contain a plurality of compounds according to the present invention.

The clinical dose of the compound of the present invention varies depending on the age, body weight, patient sensitivity, the degree of symptoms, and the like, but the effective dose is generally 0.003 g to 1.5 g per day for adults, and preferably about 0.01 g to 0.6 g. However, if necessary, an amount outside the above range can be used.

The compound of the present invention is formulated for administration by a conventional pharmaceutical means.

Specifically, tablet, capsules, granules, and pills for oral administration are prepared using excipients, for example, white sugar, lactose, glucose, starch, and mannitol binding agents, for example, hydroxypropyl cellulose, syrup; gum arabic, gelatin, sorbitol, tragacanth, methyl cellulose, and polyvinylpyrrolidone; disintegrating agents, for example; starch, carboxymethyl cellulose or its calcium salt; microcrystalline cellulose, and polyethylene glycol; smoothing agents, for example, talc, magnesium stearate or calcium, and silica; and lubricants, for example, sodium laurate, and glycerol.

Injection agents, liquids, emulsions, suspensions, syrups and aerosol agents are prepared using active component solvents, for example, water, ethyl alcohol, isopropyl alcohol, propylene glycol, 1,3-butylene glycol, and polyethylene glycol; surfactants, for example, sorbitan fatty acid ester, polyoxyethylene sorbitan fatty acid ester, polyoxyethylene fatty acid ester, polyoxyethylene ether of hydrogenated castor oil, and lecithin; suspensions, for example, carboxymethyl sodium salts, cellulose derivatives such as methyl cellulose, and natural rubbers such as tragacanth and gum arabic; preservatives, for example, paraoxybenzoic acid ester; benzalkonium chloride, and sorbite, and the like.

For the ointment which is a percutaneous absorption type preparation, for example, white petrolatum, liquid paraffin, higher alcohols, macrogol ointments, hydrophilic ointments, aqueous gel bases, and the like are used.

Suppositories are prepared using, for example, cacao fats, polyethylene glycol, lanolin, fatty acid triglyceride, coconut oil, polysorbate, and the like.

EXAMPLES

While the present invention will be described below in more detail with reference to examples, the present invention is not limited to these examples.

Here, the terms used in examples are supplemented below
PCR: polymerase chain reaction
cRNA: complementary RNA
Addgene: name of non-profit plasmid bank
DMSO: dimethyl sulfoxide
ND96 solution: the following aqueous solution 96 mM NaCl, 2 mM KCl, 1.8 mM CaCl$_2$, 1 mM MgCl$_2$, 5 mM HEPES, pH 7.4 Ba$^{2+}$: barium chloride aqueous solution (or other divalent barium salt aqueous solution) mCherry: red fluorescent protein (refer to Experimental Medicine Special Edition Vol. 35 No. 5, etc.)

Gps GFP: green fluorescent protein (refer to Japanese Journal of Pharmacological Sciences Vol. 138 (2011) Nal P13-17, etc.)

Germline transmission: germline transmission

Example 1

In order to analyze the inhibitory action of the compound (II) on the KCNJ3 N83H KACh channel, cRNA of KCNJ3 N83H or wild type KCNJ3 (KCNJ3 WT) and cRNA of wild type KCNJ5 were injected into *Xenopus laevis* oocytes to express the KACh channel, electrodes were inserted, and the channel activity was confirmed by a two-electrode voltage clamp method. By co-expressing with 0 and 7 subunits of G protein, a whole cell current was able to be directly measured via the activated KACh channel.

The coding sequence of human KCNJ3 WT was obtained by amplifying a human KCNJ3 cDNA clone (commercially available from Invitrogen) by PCR, and subcloning it into a pCS2+ vector (commercially available from Addgene). The c.247A>C mutation providingKCNJ3 N83H was introduced by site-directed mutagenesis through PCR. Similarly, the human KCNJ5 coding sequence was obtained by amplifying a human KCNJ5 cDNA clone (commercially available from Invitrogen) by PCR and subcloning it into a pCS2+ vector. The cRNAs of KCNJ3 WT, KCNJ3 N83H and KCNJ5 were synthesized from linearized cDNA using an mMESSAGE mMACHINE kit (commercially available from Life Technologies) vitro transcription. cRNA of KCNJ3 N83H or KCNJ3 WT and cRNA of wild type KCNJ5 were injected into *Xenopus laevis* oocytes together with cRNA of β and γ subunits of G protein, and incubated in an ND96 solution at 18° C. for 48 to 96 hours.

The glass pipette electrode had a resistance of 0.3 MΩ to 1.0 MΩ when filled with a 3 M potassium chloride aqueous solution. For the extracellular fluid, the pH of a test bath solution containing 40 mM potassium chloride, 50 mM sodium chloride, 3 mM magnesium chloride M, 0.15 mM niflumic acid, and 5 mMHEPES was adjusted to 7.4 with potassium hydroxide.

The whole cell current via the expressed KACh channel was measured by a two-electrode voltage clamp method using a GeneClamp 500 amplifier (commercially available from Molecular Devices). The compound (II) dissolved in DMSO, and a perfusate was prepared so that the final concentration was 0.001, 0.01, 0.03, 0.1, 1, and 10 μM. The perfusate containing the compound (II) with a low concentration was added when the amount of current was almost steady, and the amount of current was then recorded while replacing it with a perfusate with a high concentration in the same manner. When the recording was ended, Ba$^{2+}$ (3 mM) was added, and the intrinsic leak current was measured. The pulse protocol is shown in Figure. The measured data was analyzed using Clampfit 10.2 (commercially available from Molecular Devices). The IC50 value was calculated using GraphPad Prism version 5.00 (commercially available from GraphPad Software).

Figure 2:
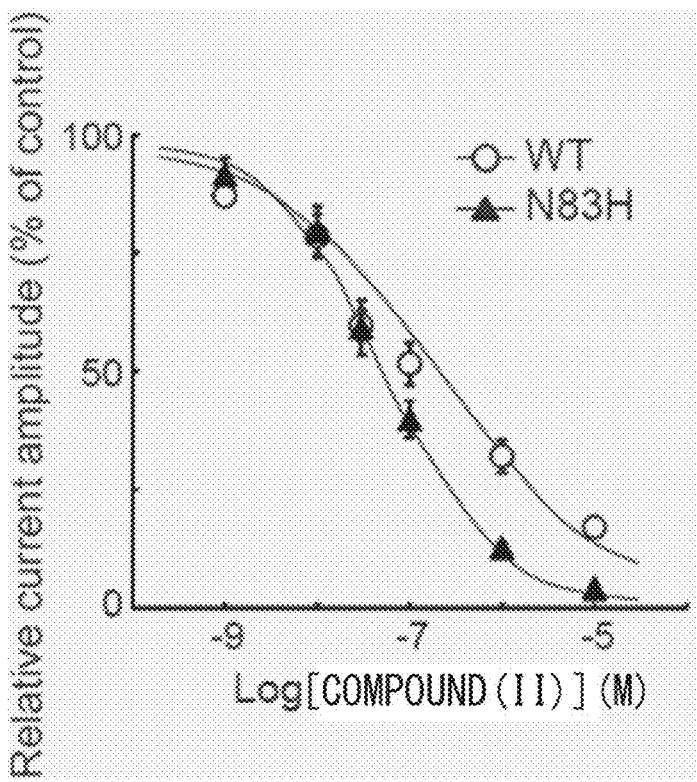
FIG. 2 is a graph showing a rate of change (%) in current amplitude (evaluated by the amount of current at a point at which a membrane potential is +20 mV) of a KCNJ3 WT KACh channel (WT) and a KCNJ3 N83H KACh channel (N83H) expressed in *Xenopus laevis* relative to the logarithm of concentration of the compound (II), which is detected using a two-electrode voltage clamp method.

The compound (II) also exhibited a concentration-dependent inhibitory effect on the KCNJ3 N83H KACh channel, its IC50 value was lower than that of the KCNJ3 WT KACh channel (N83H mutant; 50±12 nM (n=14), wild type; 230±60 nM (n=13), p<0.01), and the compound (II) exhibited higher affinity for the mutant KACh channel (FIGS. 1 and 2).

Example 2

In order to analyze the inhibitory action of the compound (II) on the KCNJ3 N83H KACh channel in vivo, a gene encoding KCNJ3 N83H was introduced into a zebrafish (*Danio rerio*) fertilized egg to prepare transgenic zebrafish into which a KCNJ3 mutation was introduced as a disease model animal. As a comparative example, zebrafish for KCNJ3 WT expression was also prepared in the same manner.

Figure 3:
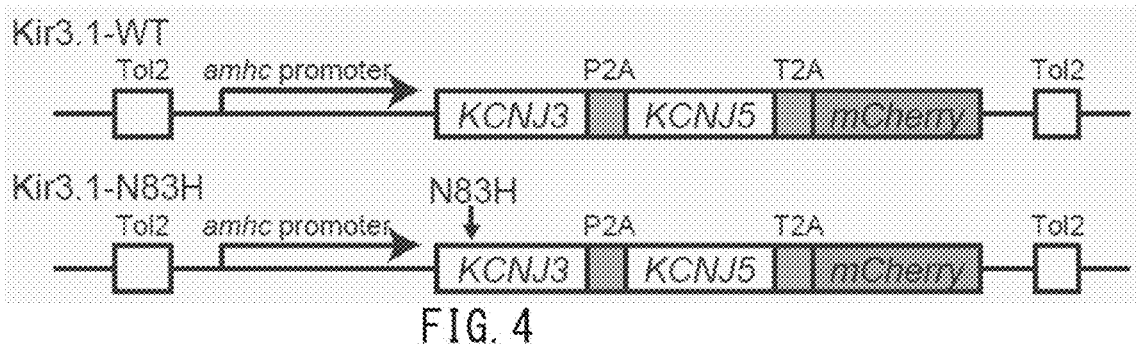
FIG. 3 shows a gene construct (Kir3.1-WT) containing a gene in which the three genes of human KCNJ3 WT, human KCNJ5 and mCherry are linked with a 2A peptide and a gene construct (Kir3.1-N83H) containing a gene in which the three genes of human KCNJ3 N83H, human KCN5 and mCherry are linked with a 2A peptide, in order to prepare transgenic zebrafish.
Figure 4:
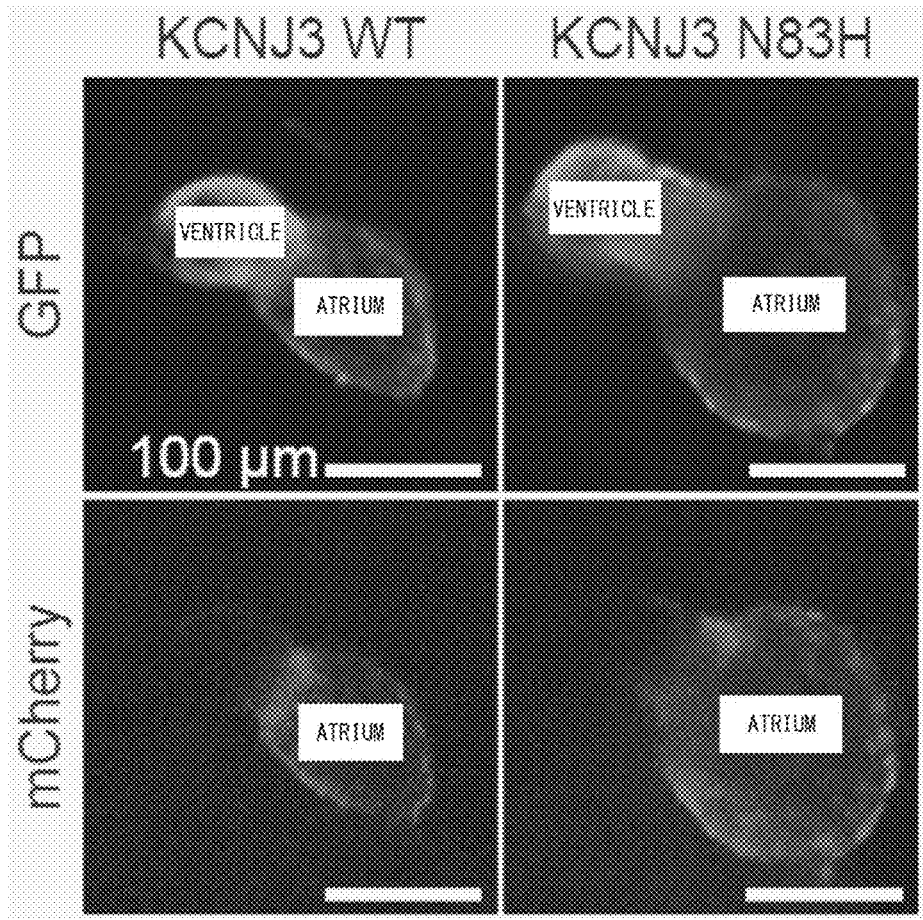
FIG. 4 shows images of the degree of expression of GFP and mCherry in the hearts of 2 day old fry of KCNJ3 WT zebrafish and KCNJ3 N83H mutant zebrafish which express GFP in the ventricle and express GFP and mCherry in the atrium, which are observed under a fluorescence microscope.
Figure 5:
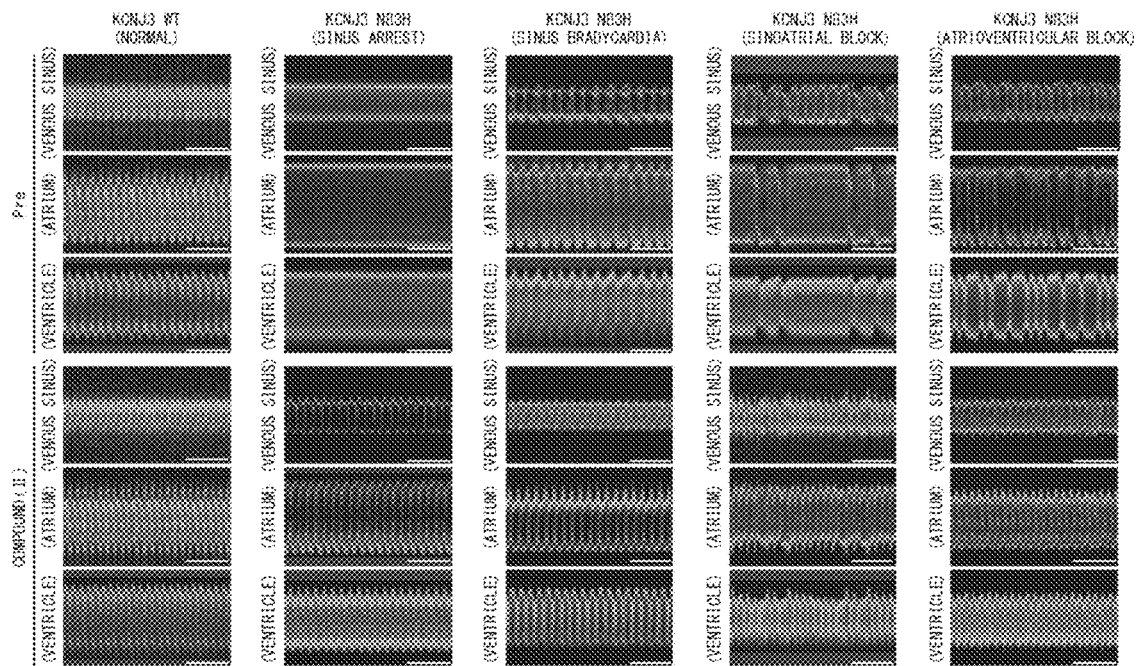
FIG. 5 shows images obtained by detailed analysis of the heart rate and pulsation rhythm using analysis software based on the video of sinus venosus, atrium, and ventricle pulsations in each zebrafish during and before application of the compound (II) to KCNJ3 WI zebrafish and KCNJ3 N83H mutant zebrafish.
Figure 6:
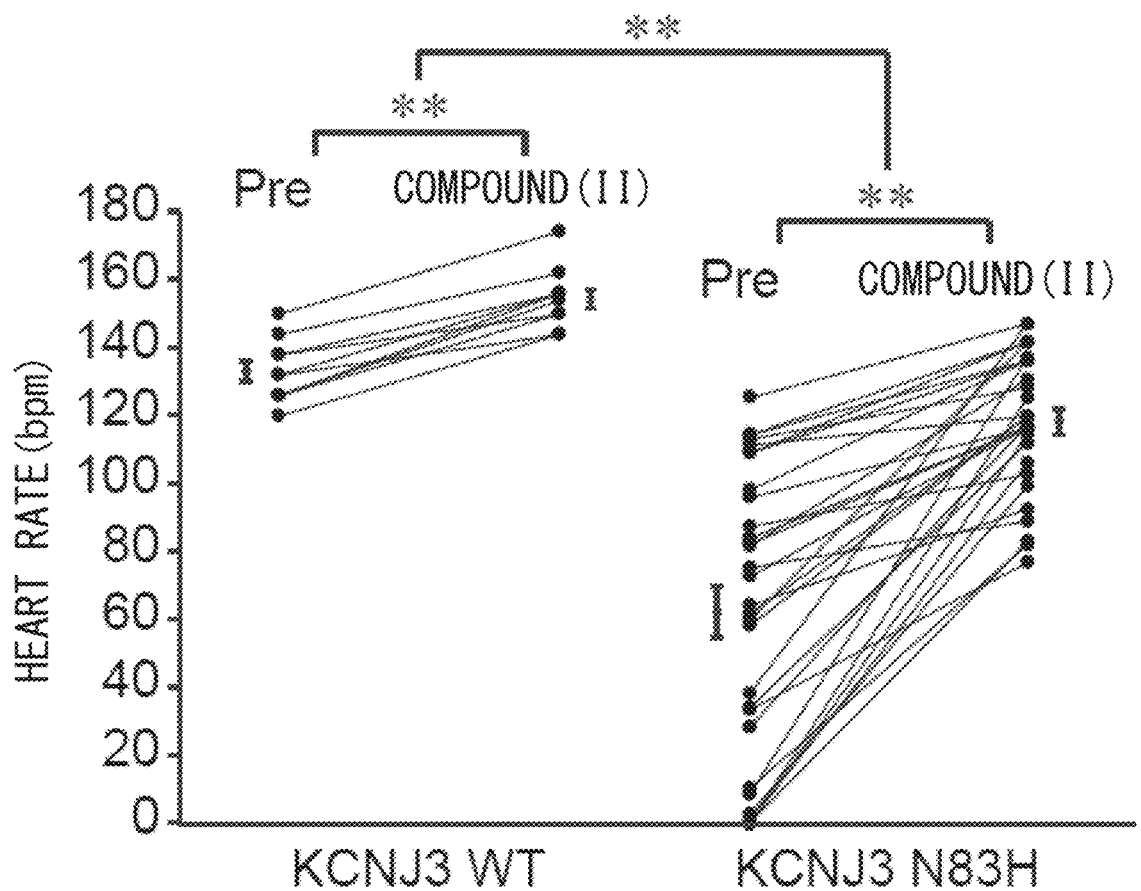
FIG. 6 is a graph in which the heart rates during and before application of the compound (II) to KCNJ3 WT zebrafish and KCNJ3 N83H mutant zebrafish are compared.

Transgenic zebrafish was prepared by a transposon transfer system using transposon Tol2. Since the cardiac KACh channel was expressed in the sinoatrial node, atrioventricular node, and atrial muscle, a gene construct in which three genes of mCherry were linked with a 2A peptide was prepared so that human KCNJ3 WT or N83H and human KCNJ5, and additionally gene introduction thereof were able to be determined under a fluorescence microscope under the control of the atrial myosin heavy chain (amhc) promoter, which expressed a target gene in zebrafish in an atrial-specific manner (FIG. 3). Next, a small amount of mRNA of the transposase encoded by Tol2 gene and this construct were simultaneously injected into the fertilized egg. When the adult fish prepared in this manner were crossed with wild type zebrafish, fish whose germline transmission was confirmed by generating fry positive for mCherry in the atrium under a fluorescence microscope were used as an F0 founder. When this F0 founder was crossed with wild type zebrafish hspGFF3A, which expressed GFP in both the ventricle and the atrium (Proceedings of the National Academy of Sciences of the United States of America. 2008; 105:1255-1260.), the heart rate and the heart pulsation rhythm were analyzed using 2 day old F1 transgenic zebrafish fry which expressed GFP in the ventricle and GFP and mCherry in the atrium (FIG. 4). Specifically, zebrafish fry was fixed on a glass bottom dish with a diameter of 35 mm with a 0.5% low-melting-point agarose gel, and the fry heart in a 0.03% sea salt aqueous solution was observed under a fluorescence microscope. Based on the video of the heart beat acquired by the camera attached to the fluorescence microscope, detailed analysis of the heart rate and pulsation rhythm was performed using original M mode analysis software (The Journal of clinical investigation. 2007, 117:2812-2824.). The heart rate was measured by the pulsation of the sinus venosus part including the sinus node. Since the expression level of mCherry in the atrium was not different between KCNJ3 WT zebrafish and KCNJ3 N83H mutant zebrafish, the expression level of the KACh channel gene was considered to be the same in both cases. In the KCNJ3 N83H mutant zebrafish, significant atrial enlargement and a bradyarrhythmia phenotype similar to human cases (sinus arrest, sinus bradycardia, sinoatrial block, atrioventricular block) were observed (FIG. 5). Next, the 0.03% sea salt aqueous solution was replaced with a 0.03% sea salt aqueous solution containing the 100 nM compound (II), and the heart beat after 1 hour was analyzed in the same manner. Surprisingly, 100 nM of the compound (II) exhibited an effect of increasing the heart rate and improving bradyarrhythmia in KCNJ3 N83H mutant zebrafish (FIGS. 5 and 6).

Here, in FIG. 5, the scale bar on the horizontal axis is 2 seconds.

The above suggests that the compound (II) had an inhibitory action on the KCNJ3 N83H KACh channel even in vivo, and could be a therapeutic agent for inherited bradyarrhythmia caused by a mutation in the KACh channel gene. In addition, it suggests that, in KCNJ3 WT zebrafish, the compound (II) caused an appropriate increase in the heart rate without causing excess tachycardia, and thus it could be effective against bradycardia not caused by a mutation in the KACh channel gene (FIG. 6).

Example 3

Figure 7:
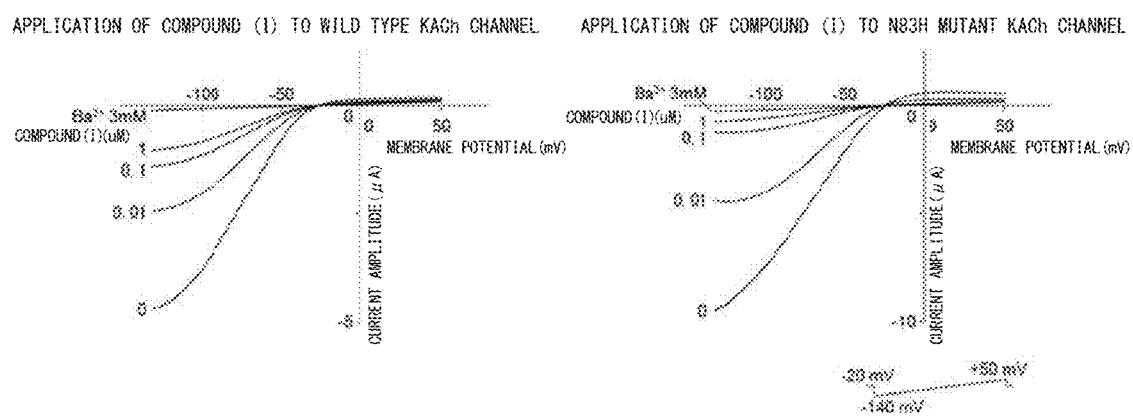
FIG. 7 shows graphs obtained by measuring an amount of current at each membrane potential when a compound (1) is applied at 3 doses of 0.01 μM, 0.1 μM and 1 μM to a KCNJ3 WT KACh channel (wild type KACh channel) and a KCNJ3 N83H KACh channel (N83H mutant channel) expressed in *Xenopus laevis* oocytes using a two-electrode voltage clamp method.
Figure 8:
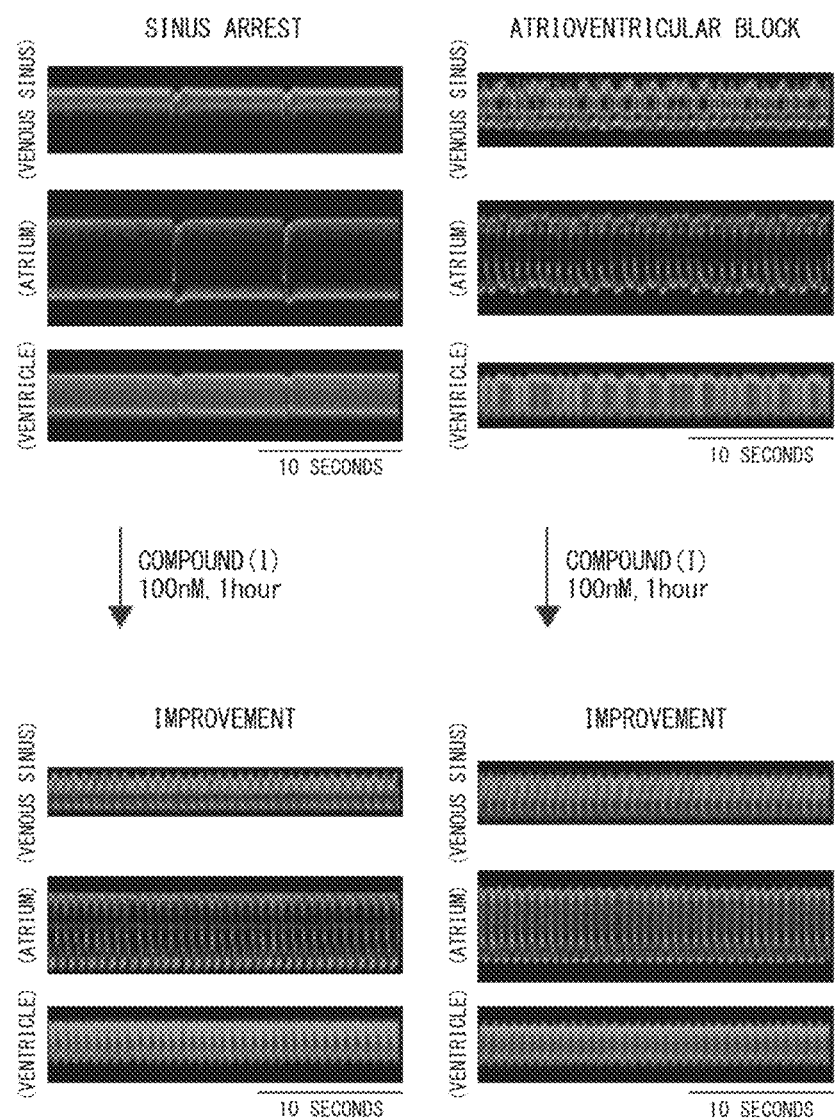
FIG. 8 shows images obtained by detailed analysis of the heart rate and pulsation rhythm using analysis software based on the video of sinus venosus, atrium and ventricle pulsations before and 1 hour after application of 100 nM of the compound (1) to KCNJ3 N83H mutant zebrafish causing sinus arrest and atrioventricular block.

For the compound (I), in the same manner as in Examples 1 and 2, that is, in the experiment with *Xenopus laevis* oocytes using a two-electrode voltage clamp method and a transgenic zebrafish model, the inhibitory effect on the KCNJ3 N83H KACh channel and the effect of increasing the heart rate and improving bradyarrhythmia in mutant zebrafish were confirmed (FIGS. 7 and 8).

The compound (I) exhibited the inhibitory effect not only on the KCNJ3 WT KACh channel but also on the KCNJ3 N83H KACh channel, but the effect was stronger on N83H than WT (FIG. 7).

In addition, the compound (I) improved the sinus arrest and atrioventricular block caused by the N83H mutation in the experiment using the transgenic zebrafish model (FIG. 8).

Example 4

In the same manner as in Example 1, the inhibitory action of the compound (I) on the KCNJ5 W101C KACh channel (W101C heterozygous mutant KACh channel) was analyzed.

In *Xenopus laevis* oocytes, in order to imitate autosomal dominant inheritance heterozygous, equimolar amounts of cRNAs of wild type KCNJ5 (KCNJ5 WT) and KCNJ5 W101C were injected together with cRNA of wild type KCNJ3 (KCNJ3 WT), the W101C heterozygous mutant KACh channel was expressed, electrodes were inserted, and the channel activity was confirmed by a two-electrode voltage clamp method.

The above human KCNJ5 cDNA clone (commercially available from Invitrogen) was amplified by PCR and subcloned it into a pCS2+ vector (commercially available from Addgene) to prepare a template, and the c.303G>C mutation providing KCNJ5 W101C was introduced by site-directed mutagenesis through PCR. The cRNAs of KCNJ5 \'VT, KCNJ5 W101C and KCNJ3 were synthesized from linearized cDNA using a mMESSAGE mMACHINE kit (commercially available from Life Technologies) in vitro transcription. Equimolar amounts of cRNA of KCNJ5 WT and KCNJ5 W101C and cRNA of wild type KCNJ3 were injected into *Xenopus oocytes* and incubated in an ND96 solution at 18° C. for 48 to 96 hours.

The glass pipette electrode had a resistance of 0.3 MΩ to 1.0 MΩ when filled with a 3 M potassium chloride aqueous solution. For the extracellular fluid, the pH of a test bath solution containing 40 mM potassium chloride, 50 mM sodium chloride, 3 mM magnesium chloride M, 0.15 mM niflumic acid, and 5 mM HEPES was adjusted to 7.4 with potassium hydroxide.

The whole cell current via the expressed KACh channel was measured by a two-electrode voltage clamp method using a GeneClamp 500 amplifier (commercially available from Molecular Devices). The compound (1) dissolved in DMSO, and a perfusate was prepared so that the final concentration was 0.01, 0.1, and 1 μM. The perfusate containing the compound (I) with a low concentration was added when the current amplitude was almost steady, and the current amplitude was then recorded while replacing it with a perfusate with a high concentration in the same manner. When the recording was ended, $Ba^{2+}$ (3 mM) was added, and the intrinsic leak current was measured. The pulse protocol is shown in Figure.

Figure 10:
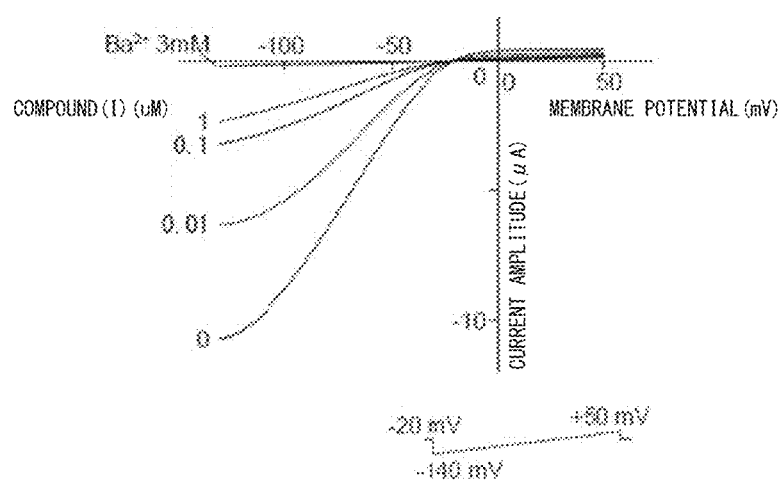
FIG. 10 is a graph obtained by measuring an amount of current at each membrane potential when the compound (I) is applied at 3 doses of 0.01 μM, 0.1 μM and 1 μM to a KCNJ5 WT/W101.0 KACh channel (W101C heterojunction mutant KACh channel) expressed in *Xenopus laevis* oocytes using a two-electrode voltage clamp method.
Figure 11:
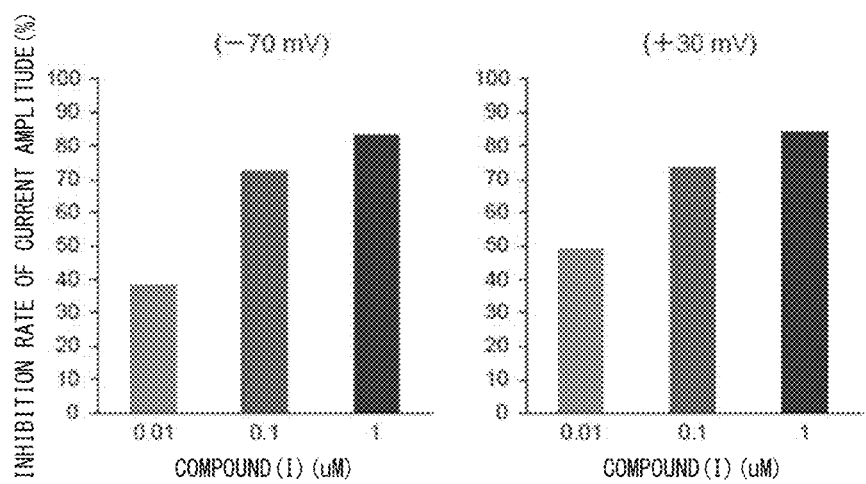
FIG. 11 shows graphs showing an inhibition rate of an amount of current when each concentration is applied at two membrane potentials of −70 mV and ±30 mV when the compound (I) is applied at 3 doses of 0.01 μM, 0.1 μM and 1 μM to a KCNJ5 WT/W101C KACh channel (W101C heterozygous mutant KACh channel) expressed in *Xenopus laevis* oocytes.

The compound (I) also exhibited a concentration-dependent inhibitory effect on the KCNJ5 WT/W101C KACh channel (W101C heterozygous mutant KACh channel) (FIG. 10, 11).

Comparative Example 1

Tertiapin-Q is a peptide having an inhibitory action on the KCNJ3 WT KACh channel (Synthesis of a stable form of tertiapin: a high-affinity inhibitor for inward-rectifier K+ channels. Jin W, Lu Z. Biochemistry. 1999 Oct. 26; 38(43): 14286-93.). Using Tertiapin-Q which inhibits the KCNJ3 WT KACh channel, an inhibitory effect on the KCNJ3 N83H KACh channel was examined.

In the same manner as in Example 2, the experiment using a transgenic zebrafish model was performed on Tertiapin-Q. Tertiapin-Q did not improve sinus arrest caused by a N83H mutation (FIG. 9).

According to this comparative experiment, it was confirmed that the therapeutic effect in the present invention was an effect specific to the compound of the present invention and a significant effect.

INDUSTRIAL APPLICABILITY

According to the present invention, the compounds (I) and (II) of the present invention can be used as the therapeutic agent for bradyarrhythmia.

The invention claimed is:

1. A method of treating bradyarrhythmia comprising administering to a patient having bradyarrhythmia a therapeutically effective amount of at least one of compound (I) and compound (II) or pharmacologically acceptable salts thereof as an active component:

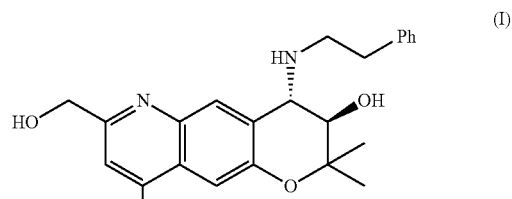

(I)

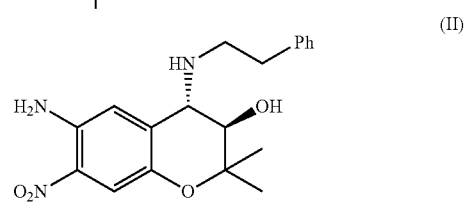

(II)

wherein Ph is a phenyl group.

2. The method according to claim 1, wherein the bradyarrhythmia is inherited bradyarrhythmia.

3. The method according to claim 1, wherein the bradyarrhythmia is any of sinus bradycardia, sinus arrest, sinoatrial block and atrioventricular block.

4. The method according to claim 1, wherein the bradyarrhythmia is any of sinus bradycardia, sinus arrest, sinoatrial block and atrioventricular block and is inherited bradyarrhythmia.

5. The method according to claim 1, wherein compound (I) or a pharmacologically acceptable salt thereof is administered as the active component.

6. The method according to claim 1, wherein compound (II) or a pharmacologically acceptable salt thereof is administered as the active component.

7. The method according to claim 1, wherein the bradyarrhythmia is an arrhythmia caused by a mutation in the 83rd amino acid from the N-terminus of a KCNJ3 protein from asparagine (N) to histidine (H).

8. The method according to claim 1, wherein the bradyarrhythmia is an arrhythmia caused by a mutation in the 101st amino acid from the N-terminus of a KCNJ5 protein from tryptophan (W) to cysteine (C).

9. The method according to claim 1, wherein the active component is administered in a pharmaceutical composition containing about 0.01% to about 99.5% of the active component by weight of the pharmaceutical composition.

10. The method according to claim 1, wherein the active component is administered in a pharmaceutical composition containing about 0.1% to about 30% of the active component by weight of the pharmaceutical composition.

11. The method according to claim 10, wherein the pharmaceutical composition is in an injectable form that includes an injection agent.

12. The method according to claim 10, wherein the pharmaceutical composition is in a form suitable for oral administration selected from the group consisting of a tablet, a capsule, a granule, a pill, a syrup, a liquid, an emulsion, and a suspension.

13. The method according to claim 1, wherein the active component is administered to the patient in an effective dose of from 0.003 g to 1.5 g per day.

14. The method according to claim 1, wherein the active component is administered to the patient in an effective dose of from 0.01 g to 0.6 g per day.

* * * * *